United States Patent
Tice

(10) Patent No.: US 7,511,623 B2
(45) Date of Patent: Mar. 31, 2009

(54) IN-RESIDENCE MONITORING SYSTEM INCORPORATING VOICE OUTPUT

(75) Inventor: Lee D. Tice, Bartlett, IL (US)

(73) Assignee: Honeywell International Inc., Morristown, NJ (US)

( * ) Notice: Subject to any disclaimer, the term of this patent is extended or adjusted under 35 U.S.C. 154(b) by 264 days.

(21) Appl. No.: 11/226,550

(22) Filed: Sep. 14, 2005

(65) Prior Publication Data

US 2007/0083089 A1 Apr. 12, 2007

(51) Int. Cl.
*G08B 23/00* (2006.01)
(52) U.S. Cl. ............... 340/573.1; 340/539.12
(58) Field of Classification Search ............. 340/573.1, 340/539.1, 539.11, 539.12, 539.16, 539.17, 340/286.07; 600/300, 485; 128/903, 904, 128/897, 905; 715/740, 744; 607/3
See application file for complete search history.

(56) References Cited

U.S. PATENT DOCUMENTS

| | | | |
|---|---|---|---|
| 5,228,449 A * | 7/1993 | Christ et al. ............... 600/504 |
| 5,564,429 A | 10/1996 | Bornn et al. ............... 128/696 |
| 5,794,219 A | 8/1998 | Brown ........................ 705/37 |
| 5,822,715 A | 10/1998 | Worthington |
| 5,828,943 A | 10/1998 | Brown |
| 5,832,448 A | 11/1998 | Brown .......................... 705/2 |
| 5,897,493 A | 4/1999 | Brown ....................... 600/300 |
| 5,899,855 A | 5/1999 | Brown ....................... 600/301 |
| 5,913,310 A | 6/1999 | Brown |
| 5,918,603 A | 7/1999 | Brown |
| 5,933,136 A | 8/1999 | Brown |
| 5,940,801 A | 8/1999 | Brown |
| 5,951,300 A | 9/1999 | Brown |
| 5,960,403 A | 9/1999 | Brown ........................... 705/2 |
| 5,985,559 A | 11/1999 | Brown |
| 5,997,476 A | 12/1999 | Brown ....................... 600/300 |
| 6,032,119 A | 2/2000 | Brown et al. ................... 705/2 |
| 6,050,940 A | 4/2000 | Braun et al. ................ 600/300 |
| 6,101,478 A | 8/2000 | Brown ........................... 705/2 |
| 6,144,837 A | 11/2000 | Quy |
| 6,151,586 A | 11/2000 | Brown |
| 6,161,095 A | 12/2000 | Brown ........................... 705/2 |
| 6,167,362 A | 12/2000 | Brown et al. ................. 703/11 |
| 6,168,563 B1 | 1/2001 | Brown ....................... 600/301 |
| 6,186,145 B1 | 2/2001 | Brown |
| 6,210,272 B1 | 4/2001 | Brown |
| 6,233,539 B1 | 5/2001 | Brown |
| 6,246,992 B1 | 6/2001 | Brown ........................... 705/2 |
| 6,248,065 B1 | 6/2001 | Brown ....................... 600/300 |
| 6,260,022 B1 | 7/2001 | Brown |
| 6,270,455 B1 | 8/2001 | Brown ....................... 600/300 |
| 6,334,778 B1 | 1/2002 | Trammell |
| 6,368,273 B1 | 4/2002 | Brown ....................... 600/300 |

(Continued)

OTHER PUBLICATIONS

PCT International Search Report from corresponding PCT application, published Aug. 10, 2007.

*Primary Examiner*—Van T. Trieu
(74) *Attorney, Agent, or Firm*—Husch Blackwell Sanders Welsh & Katz

(57) ABSTRACT

A system for monitoring health related parameters of an individual can determine the existence of one or more health related conditions that may need attention. Verbal messages, responsive to the determined condition, can be automatically transmitted via one or more communications networks to displaced recipients.

25 Claims, 1 Drawing Sheet

U.S. PATENT DOCUMENTS

| | | |
|---|---|---|
| 6,375,469 B1 | 4/2002 | Brown |
| 6,381,577 B1 | 4/2002 | Brown .......................... 705/2 |
| 6,389,301 B1 | 5/2002 | Furuya |
| 6,402,691 B1 | 6/2002 | Peddicord et al. ........... 600/300 |
| 6,612,984 B1 | 9/2003 | Kerr, II ....................... 600/300 |
| 6,705,990 B1 * | 3/2004 | Gallant et al. ............... 600/300 |
| 6,723,046 B2 | 4/2004 | Lichtenstein et al. ........ 600/300 |
| 6,893,396 B2 * | 5/2005 | Schulze et al. .............. 600/300 |
| 6,985,771 B2 * | 1/2006 | Fischell et al. ................. 607/3 |
| 7,073,129 B1 * | 7/2006 | Robarts et al. .............. 715/740 |
| 7,137,069 B2 * | 11/2006 | Abbott et al. ............... 715/744 |
| 2003/0050536 A1 | 3/2003 | Hood |
| 2005/0148828 A1 | 7/2005 | Lindsay |

\* cited by examiner

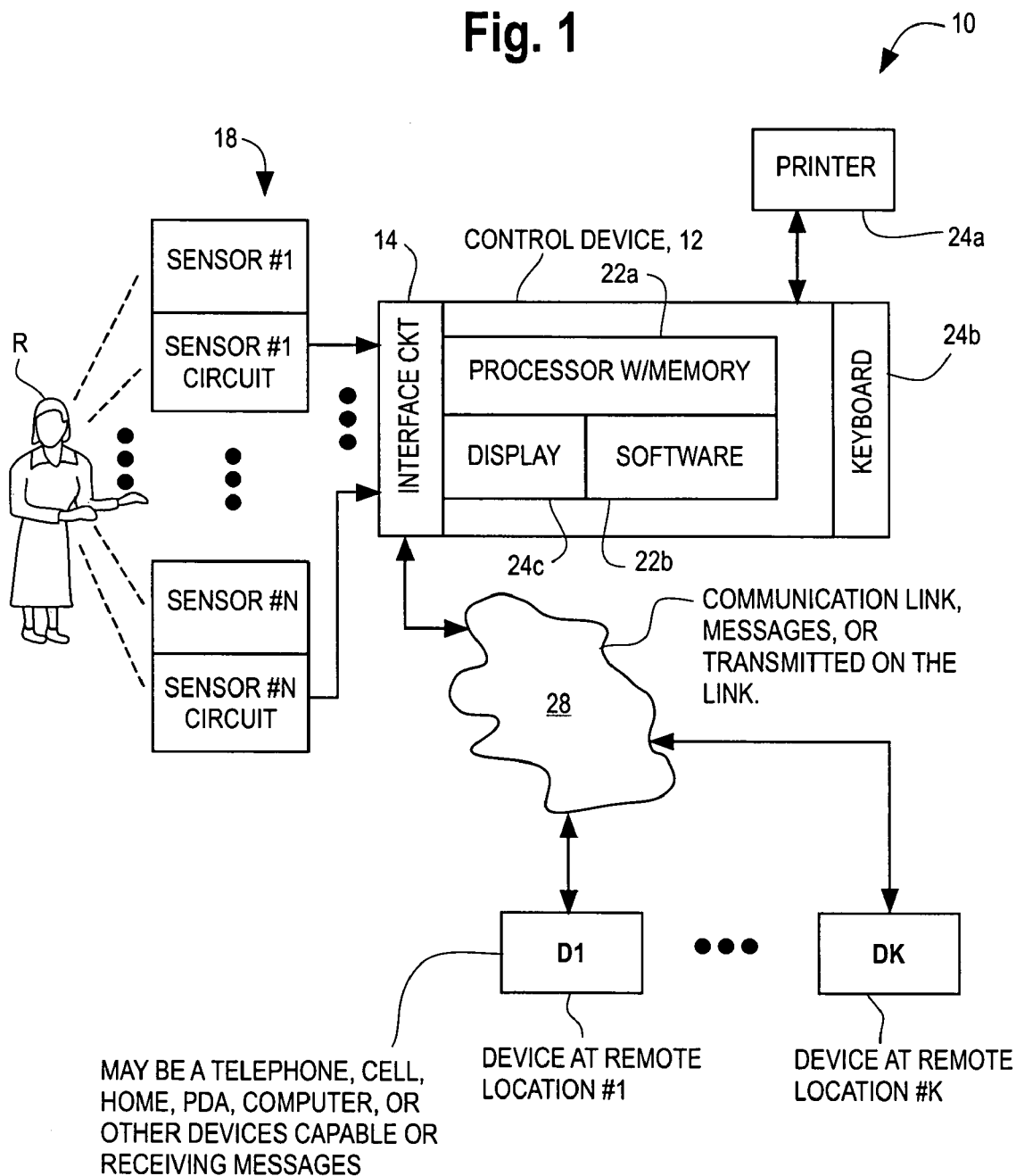

IN-RESIDENCE MONITORING SYSTEM INCORPORATING VOICE OUTPUT

FIELD

The invention pertains to systems for monitoring the health of an individual. More particularly, the invention pertains to such systems which can initiate and transmit verbal messages relative to a medical condition of the individual.

BACKGROUND

Known in-home resident or person monitoring systems often provide for the transmission of data to at least one location. This data is usually transmitted in a digital format. There is usually a computer at the receiving location that receives the digital information, decodes the information, stores the information, and compiles charts and displays for medical personnel to review.

On-going monitoring may provide updated information on a scheduled basis, once or several times during a day. If there is an emergency situation at the resident's home, there may be a delay before the medical personnel review and recognize that emergency situation. The time of response to an emergency situation may determine the difference between life and death. It therefore is extremely desirable to have the system provide an emergency response.

BRIEF DESCRIPTION OF THE DRAWING

FIG. 1 is a block diagram of a system in accordance with the invention.

DETAILED DESCRIPTION

While this invention is susceptible of embodiment in many different forms, there are shown in the drawing and will be described herein in detail specific embodiments thereof with the understanding that the present disclosure is to be considered as an exemplification of the principles of the invention and is not intended to limit the invention to the specific embodiments illustrated.

In one aspect of the invention an emergency response is facilitated by analyzing sensor inputs and determining the existence of a pre-defined condition. This determination may be made in the processor based upon pre-programmed information that has been approved or reviewed by medical personnel. In response, voice messages can be sent to other locations in addition to a central monitoring location.

The other locations can include neighbors, relatives, friends, police, fire department, etc. However, these other locations are unlikely to have decryption or equipment that can interpret digital messages. Hence, voice messages that can be easily understood by any person who understands the specific language native to the area can be provided. It is within the scope of this invention that the language of the messages may be selectable or predetermined. It is also within the scope of this invention that the language selection may be dependent upon the location that the message is being sent to.

The messages sent to a central monitoring location may be digital even though the messages sent to the other locations may be either voice or voice encoded. Voice encoded includes digitally encoding, transmitting the encoded voice to the other location in digital form, and then decoding at the other location back to audible voice to be heard by a person. One example using voice encoding would be voice over the internet protocol (VOIP).

The primary benefit of transmitting message information relating to a resident is that others are informed of the situation and may be able to provide aid faster than the emergency response personnel sent to the residence. If it is an emergency situation, then one of the other locations may be a neighbor who can be the first responder.

If the type of emergency is known to be likely to occur, then the system can be programmed and approved to provide instructions for the neighbor to follow in stabilizing the resident until medical personnel arrive. In addition, the system can alert relatives to the situation.

Preferably, the messages will contain information regarding the situation so the other locations can determine the proper response. This can be accomplished by using the computer or other processor associated with the in-home monitoring system to analyze the sensor inputs and to then transmit one or more messages that relate to that analysis.

For example, if a resident's cardiac or circulatory system sensor sends signals to the monitoring system indicating that the heart is not functioning within normal limits, the monitoring system can then form a message that describes the problem. That message can be sent to the other locations in addition to the central monitoring location. The message to the other locations may be sent in a verbal format while the message to the central monitoring location may be digital as well as verbal.

The message sent to the other locations may be pre-programmed in its entirety. In this instance, the system selects the message based upon the situation.

Alternatively, the message may be partially predetermined or in the form of stored words or verbal elements that the system can then combine to construct a message that represents the situation.

The system can also include software that is capable of forming the proper voice or text message that is transmitted. If the situation is a heart attack, then the message sent will relate to a heart attack and the importance of responding. It is also within the scope of this invention that the message will include information as an action to be taken.

Instructions could be provided as to how to obtain the stabilization procedures from the system or the stabilization procedures themselves. The system can enable the person receiving the message to select how the system will provide information to them. This makes the communication interactive.

In one aspect of the invention, if the message is received by a cell phone, the person receiving the information may request that the stabilization procedure be sent after he/she sends a signal that indicates they are now with the resident and ready to carry out the stabilization or life saving action. If they want portions of the message repeated, then they can indicate that to the system. The system can construct specific messages to guide that person through the procedures based upon the situation.

In addition to the voice signals, messages may be sent to other locations that include text decoding using equipment such as a computer or wired or wireless telephone. Text messaging is within the scope of this invention wherein the messages are formed by the system in response to the analysis of the situation by the system.

In a further aspect of the invention, the messaging function may interact with the person administering aid. In this regard, instructions can be repeated or amended by providing new information to the system. For example, the person administering aid may recognize some bleeding or other condition of the resident and then send that information back into the system. The system can automatically forward that information to a central monitoring station and medical personnel.

Verbal messaging in accordance with the invention is not limited to an emergency. The system can send routine verbal messages to other locations that are informative and represent the status of the resident.

In yet another aspect of the invention, graphical and/or sensor information may be transmitted to the other locations if it is determined that the specific location has the proper receiving equipment such as a computer or telephone capable of displaying this information. In this way, it is possible for pre-approved persons, which may include relatives, to observe the status of the resident. In addition to the central monitoring location, these pre-approved persons can also monitor the daily routine of the resident to help insure compliance with a medication schedule and sensor data recording.

In another aspect of the invention, the monitoring information in non-emergency messages may include graphical displays of the sensor values associated with the resident as well as the routines to be followed by the resident or person. The graphical displays may include upper and lower boundary limits for the sensor signals and trend information without limit. The system may analyze the situation and then select the specific graphical display or displays to transmit. The graphical display or displays can include projections of future changes as well as history information.

Any transmission of medical information would require the pre-approval of the resident. The person receiving the message may be required to provide verification codes or verification information to assess that they are the pre-approved person to have this information. The verification information may be compared with stored information in the interface unit or local monitoring system at the residence or at any remote location where information may be accessed.

In addition to providing status information regarding a person, the message(s) formed by the system may also include instructions including access information to contact a different remote location. In this way, the pre-authorized person receiving the message may obtain the information from a different remote location rather than directly from the in-residence monitoring devices.

FIG. 1 illustrates a block diagram of a system 10 which embodies the present invention. The system 10 includes control device 12 which is coupled via interface circuitry 14 to a plurality of physiological sensors 18. The sensors 18 could include temperature sensors, respiratory sensors, blood pressure sensor, other types of cardiac sensors, as well as other types of physiological sensors as would be known to those with skill in the art, all without limitation.

A control device 12 also includes control circuitry which could be implemented, at least in part, with a programmable processor 22a, and associated control software 22b. Local input/output devices could include, without limitation, a printer 24a, keyboard 24b and display device 24c.

Interface circuitry 14 also includes a circuitry for communicating via one or more communication links 28 which could include without limitation the public switched telephone network, one or more computer networks such as an intranet or an internet or combinations of the above. Software 22b in combination with the processor 22a can analyze outputs from one or more of the members of the plurality of sensors 18 and determine the presence of a condition requiring an immediate response. In responding thereto, the control device 12 can establish and forward one or more messages via network 28 to one or more remote receiving devices at a plurality of displaced locations such as device d1, d2, . . . dk. The devices di could correspond to inline telephones, cell phones, personal digital assistants, as well as one or more computers. Where the device is of the type to receive and present messages audibly such as inline telephone or cell phone, messages can be forwarded by control device 12 in an appropriate format. On the other hand, where the receiving device is a computer, pda or other type of device that has an expanded message capability, and is not limited to presenting audible messages, messages can be forwarded via the link 28 in a variety of formats including voice over internet protocol (VOIP) type format as desired. Devices receiving such messages can present same in an appropriate format to one or more persons in the vicinity of the respective device. For example, without limitation, the messaging function carried out by control device 12 can interact with a person local to the resident, concerning whom the sensors are providing information, who is administering aid. That person can communicate for example via cell phone, with the control device 12 to seek additional information and/or instructions as to how to assist the resident. Other information can be provided locally via display 24c to the individual present attempting to assist the resident.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

The invention claimed is:

1. An apparatus comprising:
   at least one physiological sensor;
   control circuitry connected to the sensor, the control circuitry including condition determining software; and
   at least two communication links between the control circuitry and at least two displaced locations, one of the at least two communication links is coupled to a remote monitoring station, the other couplable to a message receiving and transmitting device;
   wherein, responsive to information from the sensor, the control circuitry forwards at least an automatically generated verbal, condition identifying, message to the device via one link and a separate non-verbal, condition identifying, message to the monitoring station via the other communication link, and
   responsive to feedback from the device, the control circuitry automatically generates at least an additional treatment specifying verbal message and forwards the treatment specifying verbal message to the device.

2. An apparatus as in claim 1 where the software forwards a plurality of verbal messages sequentially to the device.

3. An apparatus as in claim 1 which includes software that generates local condition identifying indicia.

4. An apparatus as in claim 1 where the software communicates with the at least two displaced locations, at least in part, via a computer network of the at least two communication links.

5. An apparatus as in claim 1 where the at least two communications links are bi-directional.

6. An apparatus as in claim 5 which includes circuitry for establishing the links via one of an internet, or, an intranet.

7. An apparatus as in claim 1 which includes additional software to establish the identity of a potential recipient prior to forwarding one of the messages.

8. An apparatus as in claim 1 which includes verbal message generation circuitry.

9. A monitoring system comprising:
- at least one sensor for monitoring a physical parameter of a person and a circuit for transferring this sensor data to an interface device;
- the interface device includes a processor with software that analyzes the sensor data to, at least in part, determine the health condition of the person, the processor includes software to automatically form at least a verbal message from pre-programmed message information, where the processor forms the message in response to the determined health condition of the person; and
- at least two communication links between the device and at least two remote locations, where the interface device transmits the formed verbal message via one of the communication links, the message being transmitted to one of the at least two remote locations via one of the at least two communication links and responsive to feedback therefrom, automatically forms and transmits at least an additional verbal message and sends at least a non-verbal message to the other location.

10. A system as in claim 9 where the messages convey information verbally.

11. A system as in claim 10 where the communications links comprise at least one of an intranet or an internet.

12. A system as in claim 10 which includes software to transmit the verbal messages via the links.

13. A system as in claim 10 which includes software to transmit verbal messages bi-directionally via the links.

14. A monitoring system comprising:
- at least one sensor for monitoring a physical parameter of a person and a circuit for transferring this sensor data to an interface device, the interface device includes software to analyze the sensor data to, at least in part, determine a health condition of the person, where the software, at least in part, forms messages in response to the determined health condition of the person, at least one of the formed messages being a verbal message, and
- where the interface device transmits the formed messages to at least two displaced locations via at least two communication links, the verbal message is transmitted to at least one displaced location and responsive to feedback therefrom, the interface device transmits at least an additional verbal message to the one displaced location.

15. A system as in claim 14 where a language of messages can be selected from a group of different languages.

16. A system as in claim 14 where multiple messages can be formed and transmitted to differenta plurality of locations.

17. A system as in claim 14 where some of the messages incorporate instructions to be executed or carried out by another person receiving the respective message.

18. A system as in claim 14 where the messages comprise verbal messages.

19. A system as in claim 18 where the verbal messages incorporate a synthesized voice.

20. A system as in claim 19 where the synthesized verbal messages may be verbalized in one or more different languages.

21. A system as in claim 14 where the message is a text message.

22. A system as in claim 14 where the message is, at least in part, in digital format.

23. A system as in claim 14 where the message is, at least in part, a data message containing graphical information.

24. An apparatus comprising:
- at least one sensor;
- control circuitry connected to the sensor;
- at least two communication links; and
- at least two displaced locations wherein the control circuitry sends at least one verbal message to one of the displaced locations via one of the communication links, the control circuitry sends at least one non-verbal message to a second of the at least two displaced locations via a second of the at least two communication links, and responsive to feedback from the one displaced location, the control circuitry sends at least one patient treatment verbal message to the one displaced location.

25. A method of monitoring the health of an individual, comprising:
- sensing physiological data from the individual;
- creating a verbal message and a non-verbal message from the sensed data;
- sending the verbal message to one displaced location via one communication link;
- sending the non-verbal message to a second displaced location via a second communication link, and
- responsive to feedback from the one displaced location, sending at least a patient treatment verbal message to the one displaced location.

* * * * *